(12) United States Patent
Schraga

(10) Patent No.: US 6,346,114 B1
(45) Date of Patent: Feb. 12, 2002

(54) ADJUSTABLE LENGTH MEMBER SUCH AS A CAP OF A LANCET DEVICE FOR ADJUSTING PENETRATION DEPTH

(75) Inventor: Steven Schraga, Surfside, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 0 days.

(21) Appl. No.: 09/095,905

(22) Filed: Jun. 11, 1998

(51) Int. Cl.$^7$ ............................................ A61B 17/14
(52) U.S. Cl. ...................... 606/182; 411/259; 411/190; 411/294; 411/299; 74/89.15; 74/459; 74/526; 74/527
(58) Field of Search .................. 606/181, 182, 606/184; 89/14.05, 14.3, 14.2, 14.4; 74/826, 815, 813, 424, 89.15, 459, 527; 411/310, 311, 294–299, 940–941, 949

(56) References Cited

U.S. PATENT DOCUMENTS

| | | | |
|---|---|---|---|
| 676,678 A | * | 6/1901 | Ellifrits ...................... 411/227 |
| 1,135,465 A | | 4/1915 | Pollock |
| 2,848,809 A | | 8/1958 | Crowder |
| 3,589,213 A | * | 6/1971 | Gourley ...................... 74/826 |
| 4,257,561 A | | 3/1981 | McKinney |
| 4,388,925 A | | 6/1983 | Burns |
| 4,426,105 A | | 1/1984 | Plaquin et al. |
| 4,785,858 A | | 11/1988 | Valentini |
| 4,834,667 A | | 5/1989 | Fowler et al. |
| 4,858,607 A | | 8/1989 | Jordan et al. |
| 4,895,147 A | | 1/1990 | Bodicky et al. |
| 4,924,879 A | | 5/1990 | O'Brien |
| 5,304,193 A | | 4/1994 | Zhadanov |
| 5,318,584 A | | 6/1994 | Lange et al. |
| 5,324,303 A | | 6/1994 | Strong et al. |
| 5,454,828 A | | 10/1995 | Schraga |
| 5,464,418 A | | 11/1995 | Schraga |
| 5,509,345 A | * | 4/1996 | Cyktich ...................... 89/14.05 |
| 5,554,166 A | | 9/1996 | Lange et al. |
| 5,613,978 A | | 3/1997 | Harding |
| 5,628,764 A | | 5/1997 | Schraga |
| 5,628,765 A | | 5/1997 | Morita |
| 5,730,753 A | | 3/1998 | Morita |
| 5,873,887 A | | 2/1999 | King et al. |
| 5,984,940 A | | 11/1999 | Davis et al. |

FOREIGN PATENT DOCUMENTS

CA           523078           3/1956

OTHER PUBLICATIONS

Sutor et al., "Bleeding from Standardized Skin Punctures: Automated Technic for Recording Time, Intensity, and Pattern of Bleeding ", A.J.C.P., vol. 541–549 (May 1971).

* cited by examiner

Primary Examiner—Henry J. Recla
Assistant Examiner—Vy Q. Bui
(74) Attorney, Agent, or Firm—Greenblum & Bernstein, P.L.C.

(57) ABSTRACT

Adjustable length element includes a first member having threads and a second member having threads. The adjustable length member also includes at least one protrusion on one of the first member and the second member, with the at least one protrusion being capable of engaging and disengaging at least one stop associated with the threads of the other of the first member and the second member as the first member and the second member are rotated relative to each other. A lancet device includes a housing, a needle holding member in the housing for holding a lancet, a biasing element for biasing the needle holding member toward an extended position, and a trigger for releasing the needle holding member from a retracted position. The lancet device also includes a cap for covering the housing and for positioning the lancet device relative to a skin surface, the cap including a first cap member having threads and a second cap member having threads. The cap further includes at least one protrusion on one of the first cap member and second cap member, with the at least one protrusion being capable of engaging and disengaging at least one stop in the threads of the other of the first cap member and the second cap member as the first cap member and the second cap member are rotated relative to each other.

26 Claims, 10 Drawing Sheets

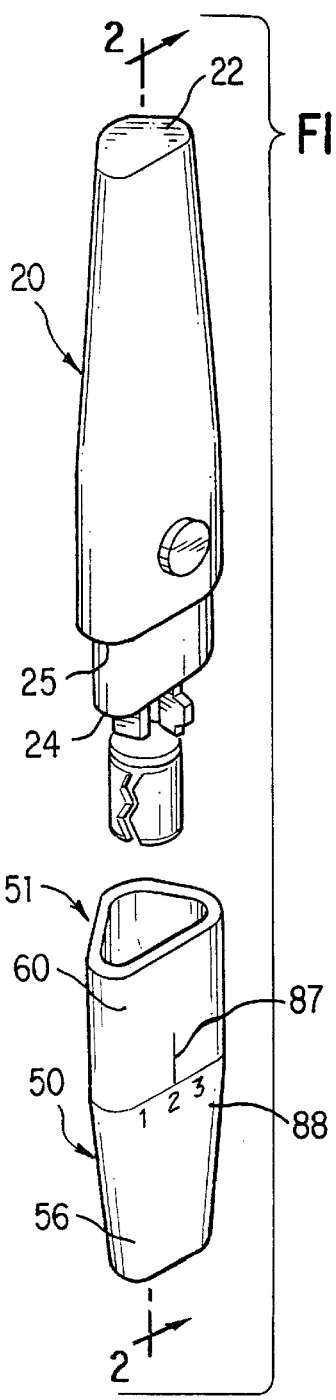
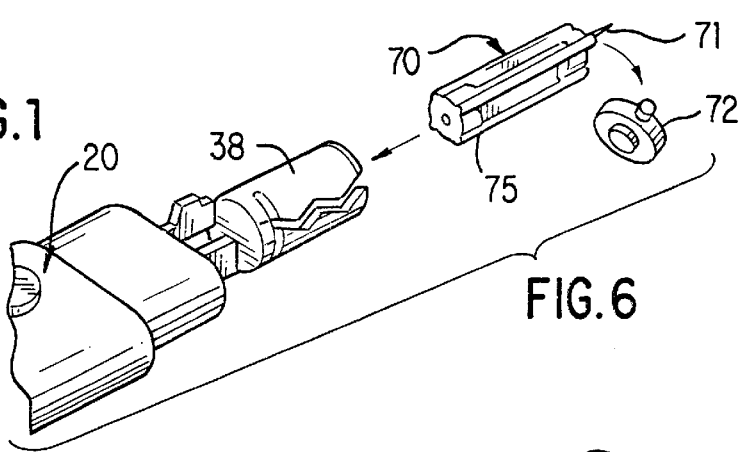
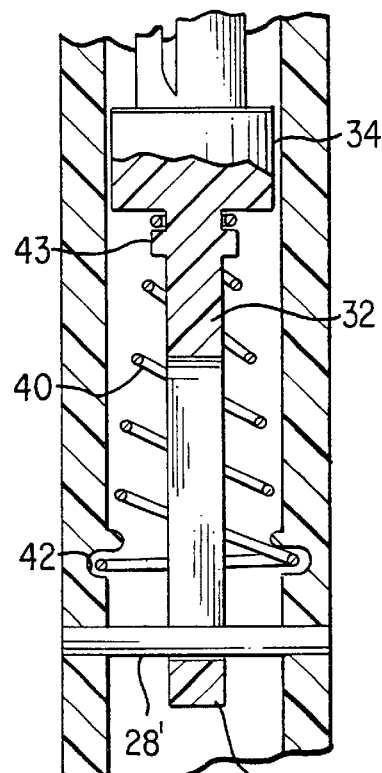
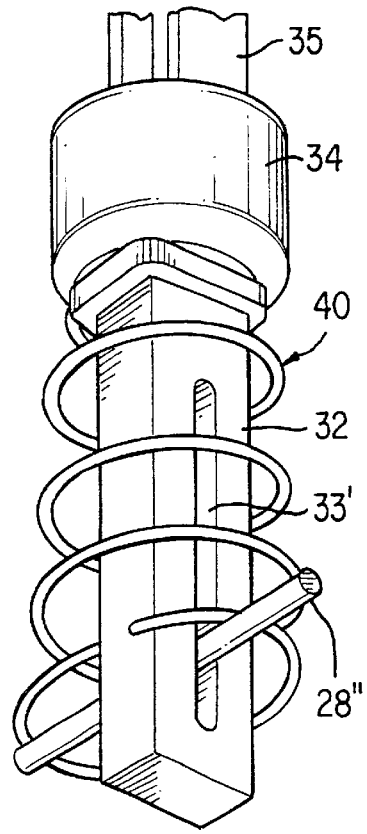
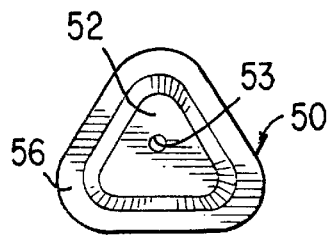

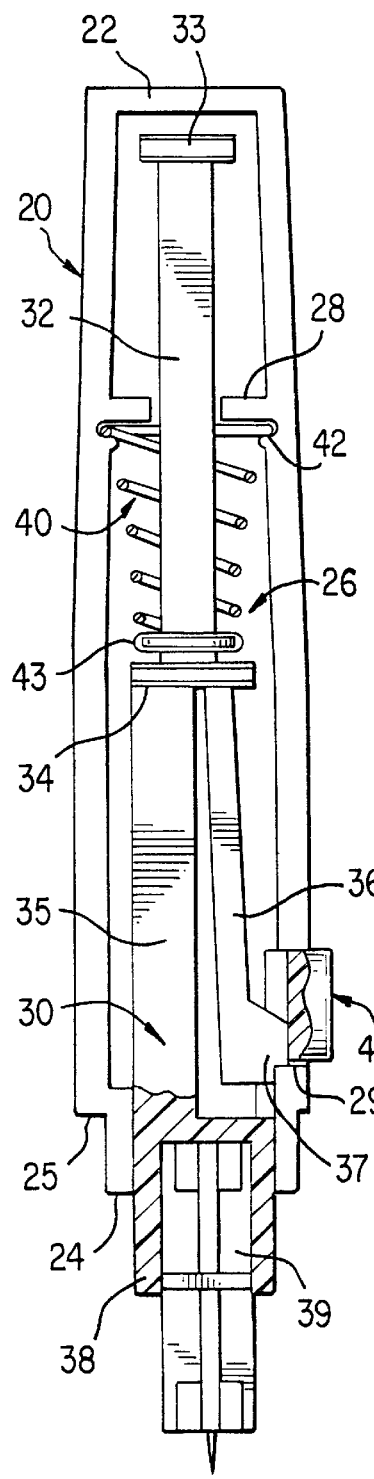
FIG. 2
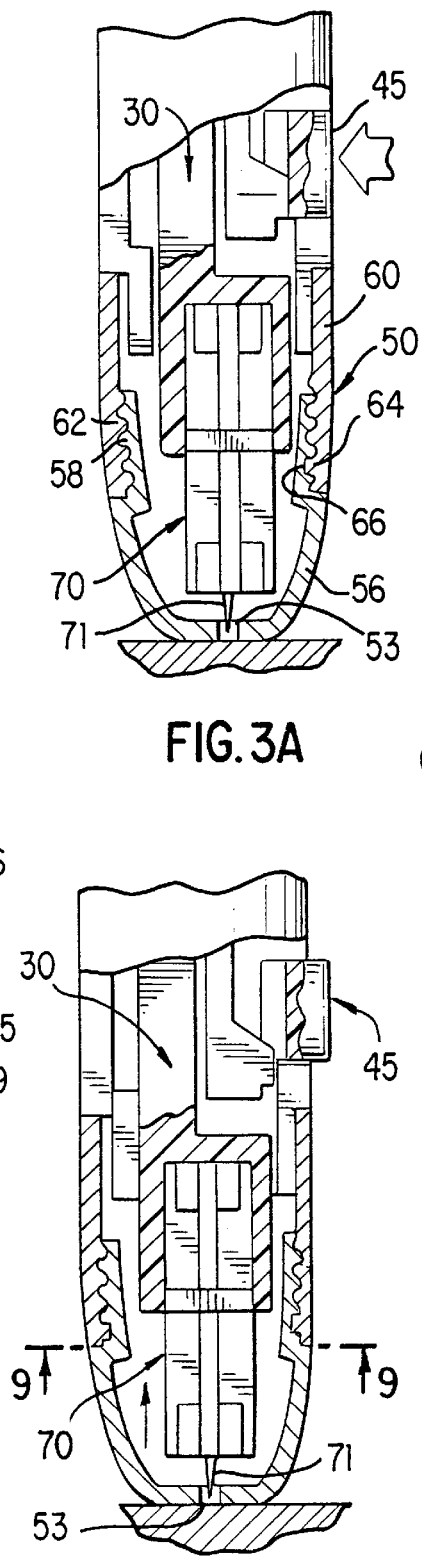
FIG. 3A
FIG. 3D
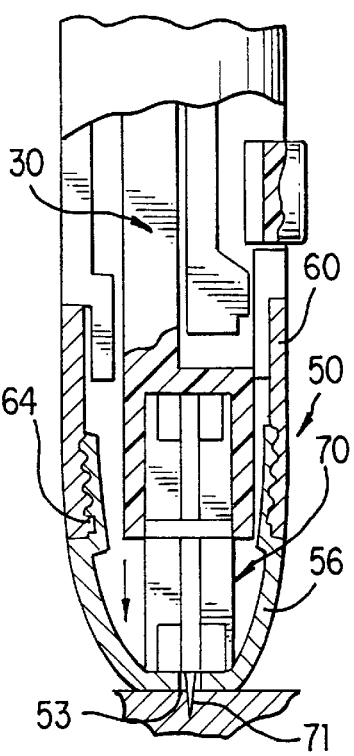
FIG. 3B
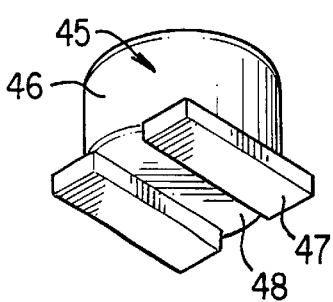
FIG. 4

ADJUSTABLE LENGTH MEMBER SUCH AS A CAP OF A LANCET DEVICE FOR ADJUSTING PENETRATION DEPTH

CROSS-REFERENCE TO RELATED APPLICATION

The present application expressly incorporates by reference herein the entire disclosure of U.S. application Ser. No. 09/095,902, entitled "Lancet Having Adjustable Penetration Depth", which is concurrently filed with the present application.

BACKGROUND OF THE INVENTION

1. Field of the Invention

The present invention relates to a member whose length is adjustable. The adjustable length member is easy to manipulate and adjust. The present invention is especially directed to an adjustable length member which is part of a lancet device to enable the lancet to have an adjustable penetration depth. The lancet device is adapted to be substantially inexpensive to manufacture and easy and safe to use by physically impaired individuals who take their own blood samples.

2. Description of Background Information

The field relating to disposable and reusable lancet devices is substantially crowded. U.S. Pat. No. 5,464,418 to SCHRAGA, the disclosure of which is incorporated by reference herein in its entirety, discloses a reusable lancet device having an elongate triangular housing and triangular cap segment.

Lancets which allow adjustment of the penetration depth include U.S. Pat. No. 5,318,584 to LANGE et al., the disclosure of which is incorporated by reference herein in its entirety. This document discloses a blood lancet device for withdrawing blood for diagnostic purposes. The penetration depth of this blood lancet device may be adjusted by adjusting the position of a sealing cap relative to a housing.

U.S. Pat. No. 4,924,879 to O'BRIEN, the disclosure of which is incorporated by reference herein in its entirety, discloses a blood lancet device. The penetration depth may be adjusted by adjusting the position of a skin surface sensor which may be a small socket head screw.

U.S. Pat. No. 5,613,978 to HARDING, the disclosure of which is incorporated by reference herein in its entirety, discloses an adjustable tip for a lancet device. The penetration depth of this lancet may be adjusted by adjusting the position of an outer cylindrical sleeve relative to an inner sleeve.

U.S. Pat. No. 4,895,147 to BODICKY et al., the disclosure of which is incorporated by reference herein in its entirety, discloses a lancet injector which includes an elongate tubular housing with a penetration depth selector provided thereon. Rotation of the penetration depth selector causes a control member to contact different contact edges to thereby control the distance that a lancet tip protrudes through a central opening.

U.S. Pat. No. 1,135,465 to POLLOCK, the disclosure of which is incorporated by reference herein in its entirety, discloses a lancet. The distance that a plunger is allowed to move forward may be changed by an adjustable movement limiting or regulating collar.

Canadian Patent No. 523,078, the disclosure of which is incorporated by reference herein in its entirety, discloses a surgical device for use in the treatment of snake bites. The surgical device includes a lance or blade whose penetration depth may be adjusted by inserting or removing a stop bar from the path of the lance or blade.

SUTOR et al., "Bleeding from Standardized Skin Punctures: Automated Technic for Recording Time, Intensity, and Pattern of Bleeding", A.J.C.P., Vol. 55, pp. 541–549 (May 1971), the disclosure of which is incorporated by reference herein in its entirety, discloses a Mayo automatic lancet. A knurled thumb screw allows adjustment of depth of cut by regulating distance between a plunger and a striking head by means of a millimeter scale.

Although there are several devices which allow adjustment of the penetration depth, there are important factors relating to the safe and effective use of lancet assemblies which have not been addressed by such devices. Specifically, there is a need for a lancet device having an adjustable penetration depth whose penetration depth adjustment mechanism is reliable and difficult to accidentally change.

SUMMARY OF THE INVENTION

The present invention is directed toward an adjustable length member which is easy to manipulate and adjust.

For example, the present invention may be directed to a lancet device to be utilized with a lancet whose penetration depth is adjustable.

It is an object of the present invention to provide a lancet device which has an adjustable penetration depth. The penetration depth may be adjusted by adjusting the length of a cap which is comprised of two threaded cap members.

It is an object of the present invention to provide a lancet device which is substantially cost effective to manufacture due to a small number of individual pieces to be put together, yet will still be substantially safe during use.

Still another object of the present invention is to provide a lancet device which provides for facilitated and effective cap positioning by impaired individuals.

Yet another object of the present invention is to provide a lancet device which is comfortably positionable within a user's hand and will not roll around within a user's hand or on a flat surface.

A further object of the present invention is to provide an lancet device which does not necessitate that an exteriorly exposed plunger assembly be utilized in order to position the lancet in a retracted, ready-to-use position.

Further, the device of the present invention is designed to be utilized by individuals to do their own routine blood test such as individuals who do home monitoring of their blood, such as diabetes patients. As a result, the present invention requires precise adaptation to make it effective yet safe for the user. As a result, the device of the present invention is comprised of a small number of individual pieces, thereby making the lancet device easier and substantially more cost effective to manufacture and provide for use by patients, without compromising any of the safety needs and, in fact, increasing the safety of use.

In accordance with one aspect, the present invention is directed to an adjustable length element, comprising: a first member having threads; a second member having threads; at least one protrusion on one of the first member and the second member, the at least one protrusion being capable of engaging and disengaging at least one stop associated with the threads of the other of the first member and the second member as the first member and the second member are rotated relative to each other.

In accordance with another aspect, the at least one stop comprises at least one recess.

In accordance with still another aspect, the at least one stop comprises at least one projection.

In accordance with still another aspect, the threads of the other of the first member and the second member comprise a groove and a ridge, and wherein the at least one stop is located in the groove.

In accordance with another aspect, the threads of the other of the first member and the second member comprise a groove and a ridge, and wherein the at least one stop is located in the ridge.

In accordance with another aspect, the at least one protrusion is connected to a button for releasing the at least one protrusion from the at least one stop.

In accordance with another aspect, the at least one protrusion is biased into the at least one stop.

In accordance with another aspect, the present invention is directed to a lancet device, comprising: a housing; a needle holding member in the housing for holding a lancet; a biasing element for biasing the needle holding member toward an extended position; a trigger for releasing the needle holding member from a retracted position; and a cap for covering the housing and for positioning the lancet device relative to a skin surface, the cap comprising a first cap member having threads and a second cap member having threads, the cap further comprising at least one protrusion on one of the first cap member and second cap member, the at least one protrusion being capable of engaging and disengaging at least one stop in the threads of the other of the first cap member and the second cap member as the first cap member and the second cap member are rotated relative to each other.

In accordance with another aspect, the at least one protrusion comprises at least one nipple.

In accordance with yet another aspect, the at least one protrusion comprises at least one spring-biased ball.

In accordance with still another aspect, the at least one protrusion is on an interior of the cap.

In accordance with another aspect, the at least one protrusion comprises a plurality of protrusions.

In accordance with still another aspect, the first cap member comprises a surface allowing passage of the lancet into a surface to be punctured, such as the skin, the surface having an opening for a needle in the needle holding member to pass through, and wherein the at least one protrusion is on the second cap member.

In accordance with yet another aspect, the first cap member comprises a surface for allowing passage of the lancet into a surface to be punctured, such as the skin, the including an opening for a needle in the needle holding member to pass through, and wherein the at least one protrusion is on the first cap member.

In accordance with another aspect, a length of the cap is adjustable by rotation of the first cap member relative to the second cap member for adjusting a penetration depth of a needle in the needle holding member.

BRIEF DESCRIPTION OF THE DRAWINGS

The present invention is further described in the detailed description which follows, in reference to the noted plurality of non-limiting drawings, and wherein:

FIG. 1 is a partially exploded perspective view of the lancet device of the present invention.

FIG. 2 is a cross-sectional view along line 2—2 of FIG. 1.

FIGS. 3A, 3B, 3C, and 3D are isolated, cross-sectional views of the lancet device illustrating the functioning of the lancet.

FIG. 4 is an isolated view of the trigger button of the lancet device of the present invention.

FIG. 5 is a bottom plan view of the triangular cap of the lancet device of the present invention.

FIG. 6 is an isolated perspective view of the lancet device illustrating the positioning of a disposable lancet therein.

FIG. 7 is an isolated cross-sectional view illustrating the positioning of the biasing element of the lancet device according to one embodiment of the present invention, wherein the needle holding member is shown in its fully extended position.

FIG. 8 is an isolated perspective view of a second embodiment of the stopper of the lancet device.

Like reference numerals refer to like parts throughout the several views of the drawings.

DETAILED DESCRIPTION

Figure 3C:
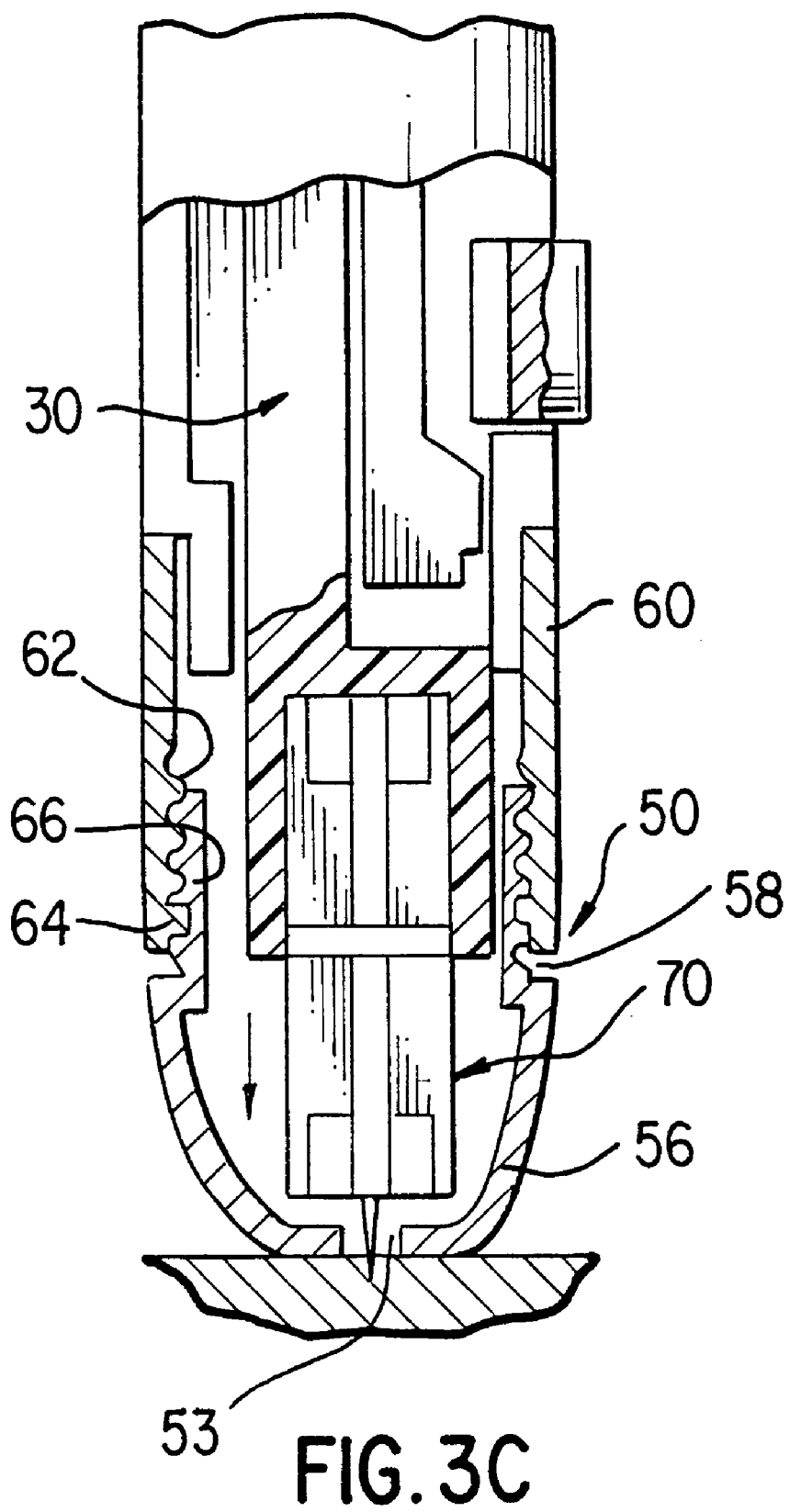

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

Before referring to the Figures, a broad overview of preferred aspects of the invention is provided. An adjustable length element of the present invention includes a first member having threads and a second member having threads. At least one protrusion on one of the first member and the second member is capable of engaging and disengaging at least one stop associated with the threads of the other of the first member and the second member as the first member and the second member are rotated relative to each other. Moreover, the at least one protrusion may also be associated with the threads.

In particular, the adjustable length element of the present invention may be directed to a cap of a lancet device, such as a reusable lancet device, for adjusting the penetration depth of the lancet. The lancet device includes an elongate housing, which is preferably triangular, adapted to fit within the user's hand. This housing includes a first end, which can be closed or open, an open second end, and an elongate channel therein which extends from the first end to the second end.

Disposed within this elongate channel is an elongate needle holding member. This needle holding member is movable between a cocked, retracted position and an extended position. The needle holding member is structured to hold a disposable lancet therein, such that a point thereof extends away from the needle holding member.

A biasing element is disposed within the housing. The biasing element is adapted to urge the needle holding member into an extended position for penetrating a user's skin when not held in a retracted position.

The lancet device also includes a cap, which is preferably triangular and tapers to a circular portion, with an open first side and a closed second side containing a piercing opening therein. The open first side is adapted to be matingly fitted over the open second end of the housing, thereby containing the needle holder member and disposable lancet therein. When in a cocked, retracted position, or after use, the needle holding member is disposed such that the point of the disposable lancet is concealed within the cap. During use, upon release by the trigger, the needle holding member is immediately moved to the extended position wherein the point of the disposable lancet will momentarily extend through a piercing opening into a piercing position which punctures a hole in a user's skin and then retracts back within the cap.

According to the present invention, the cap includes a first cap member having threads and a second cap member having threads for engaging the threads of the first cap member. The cap further includes at least one protrusion on either the first cap member or the second cap member. The protrusion is capable of engaging and disengaging at least one stop associated with the threads of the other of the first cap member and the second cap member as the first cap member and the second cap member are rotated relative to each other.

By rotating the first cap member and the second cap member relative to each other, the length of the cap is adjusted such that the penetration depth is adjusted. By engaging and disengaging the at least one stop, the protrusion temporarily fixes the length of the cap to temporarily fix the penetration depth. Adjusting the penetration depth is important because different penetration depths are necessary to draw blood from different people due to differences in skin thickness, differences in healing time of the skin puncture, differences in pain tolerances, and differences in the amount of blood needed to be drawn.

The present invention also preferably includes a stopper system to prevent axial movement of the needle holding member within the housing. Utilizing the stopper system, the needle holding member will always be retained within the elongate channel of the housing despite its movement from the cocked, retracted position to the extended position.

The needle holding member is held in the cocked, retracted position, and accordingly a biasing element is held in a retracted, compressed position, until released by a trigger. The trigger releases the needle holding member from the cocked, retracted position which results in an immediate movement of the needle holding member to the extended position as a result of the functioning of the biasing element.

Moreover, before referring to the Figures, the illustrated reusable lancet device is similar to that disclosed in U.S. Pat. No. 5,464,418 to SCHRAGA, the disclosure of which is herein incorporated by reference in its entirety.

FIGS. 1–14 illustrate several embodiments of a reusable lancet device whose penetration depth may be adjusted by adjusting the length of a cap via a threaded connection between two cap members with one of the cap members having at least one protrusion for engaging and disengaging at least one stop associated with the threads of the other cap member. The reusable lancet device 10 is preferably formed of a lightweight, rigid or semi-rigid, and substantially inexpensive plastic material and is adapted for use with a standard type of disposable lancet 70. The reusable lancet device 10 includes an elongate, substantially triangular shaped housing 20. The housing 20 includes the substantially triangular shape, with slightly rounded corners, such that it will be easy to manipulate and will not unnecessarily roll around within a user's hand, especially if the user is sick, old, or otherwise impaired. Although the most preferred shape of the housing 20 is triangular, the housing 20 may be other shapes such as round but is preferably any shape that will not roll around on a flat surface such as D-shaped, rectangular, or octagonal.

The elongate triangular housing 20, as illustrated in FIG. 2, includes a closed first end 22, an open second end 24, and an elongate channel 26. Further, the housing 20 is preferably molded of two halves to be joined together, so as to facilitate manufacture. The elongate channel 26 extends from the closed first end 22 to the open second end 24.

Slidably positioned within the channel 26 is an elongate needle holding member 30. This needle holding member 30, which is movable between a cocked, retracted position, illustrated in FIG. 2, and an extended position, illustrated in FIG. 3B, includes three segments. Specifically, the needle holding member 30 is formed of a distal segment 32, a central segment 35, and a proximal segment 38.

The proximal segment 38, which protrudes from the open second end 24 of the housing 20 is adapted to hold the disposable lancet 70 therein. Specifically, the disposable lancet 70 includes a main body 75 and a point 71, which until use is contained within a protective cap 72. When used, the body 75 is inserted into a cavity 39 of the proximal segment 38, as illustrated in FIG. 2, then the protective cap 72 is pulled or twisted from the point 71. Although the cavity 39 and disposable lancet 70 are shown as being round, the cavity 39 and disposable lancet 70 could be any other shapes, such as square, octagonal, etc., so long as the disposable lancet can be engaged in the cavity 39. The disposable lancet 70 is held in the proximal segment 38 such that the point 71 points away from the housing and such that sliding movement of the needle holding member 30 will result in corresponding movement of the disposable lancet 70.

To contain and shield the exposed point 71 of the disposable lancet 70, a triangular cap 50 is included. The triangular cap 50 includes an open first side 51 and a closed second side 52. The cap 50 is adapted to have substantially the same configuration as the housing 20 and is sized such that the open first side 51 may be matingly fitted over the open second end 24 of the housing 20. Of course, although the cap 50 is shown as being triangular, the cap 50 may be other shapes depending upon the shape of the housing 20.

Further, the open second end 24 of the housing 20 extends from a lip 25 formed in the housing 20, the lip 25 being disposed such that the open first side 51 of the cap 50 slides onto the housing 20 over the open second end 24 of the housing 20 and will abut the lip 25 providing a smooth contoured finish. The cap 50 will be removably fitted on the housing 20 preferably through corresponding proportioning of an interior dimension of the open first side 51 of the cap 50 relative to the open second end 24 of the housing 20, but alternatively engagement ridges or a similar removable fastener system may be included to secure the cap 50 on the housing 20. Other removable fastener systems include threads, locking clips, and locking buttons.

Disposed in the closed second side 52 of the cap 50 is a piercing opening 53. The piercing opening 53 is positioned such that when the needle holding member 30, containing a disposable lancet 70 therein, is moved to its fully extended position, the point 51 of the disposable lancet 70 will protrude through the piercing opening 53 to puncture a desired surface.

Figure 9:
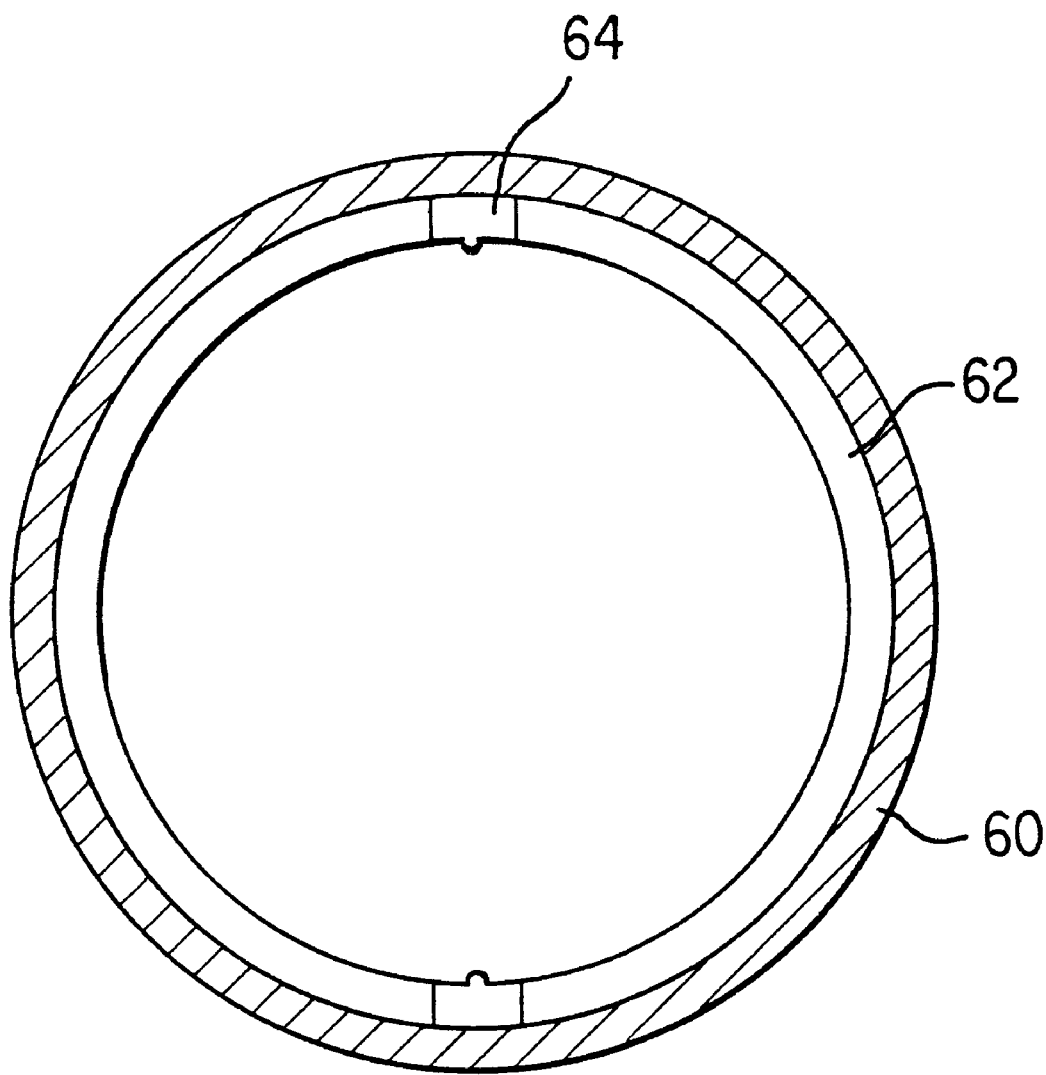
FIG. 9 is a cross-sectional view taken along line 9—9 of FIG. 3D with only the second cap member being shown.

In the embodiment shown in FIGS. 1–11, the cap 50 includes a first cap member 56 having threads 58 and a second cap member 60 having threads 62. The cap 50 further includes at least one protrusion 64 on the first cap member 56 (FIG. 9). The protrusions 64 are preferably formed of a resilient material and may be the same material which forms the housing 20.

Figure 10:
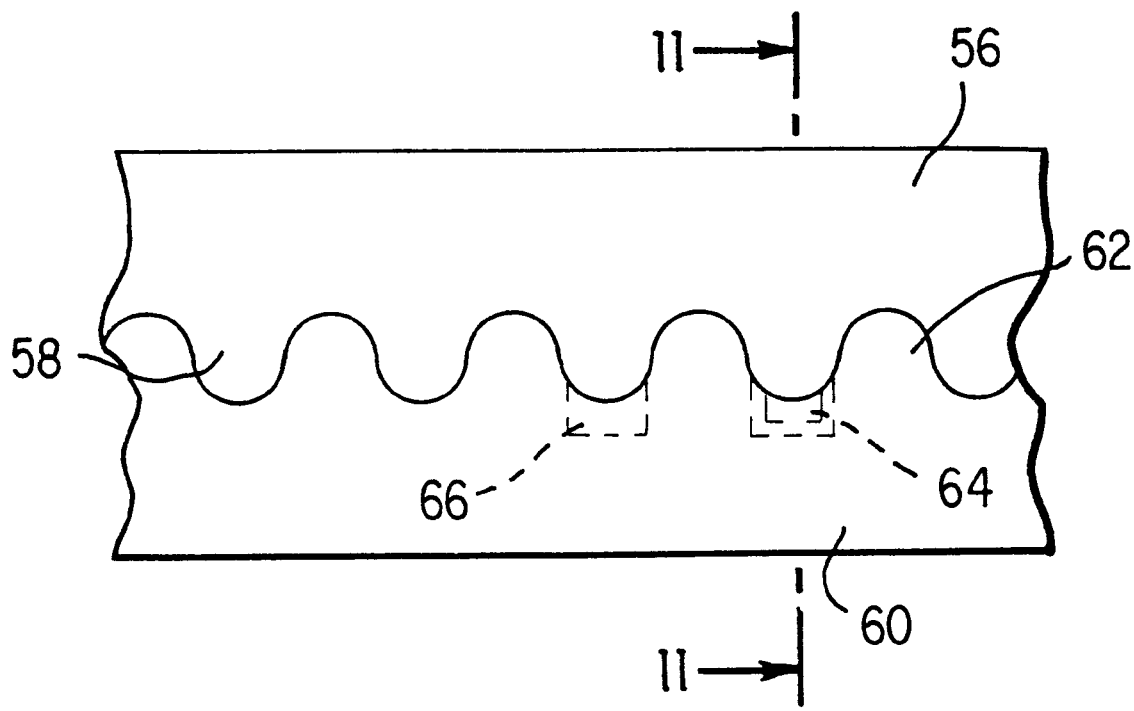
FIG. 10 is a cross-sectional view taken along a portion of line 2—2 of FIG. 1.

The protrusions 64 are capable of engaging and disengaging recesses 66 in the threads 62 of the second cap member 60 as the first cap member 56 and the second cap member 60 are rotated relative to each other, (FIG. 10). The recesses 66 are designed to facilitate engagement and disengagement with the protrusions 64. In particular, the recesses may be tapered, rounded, or oval.

Figure 11:
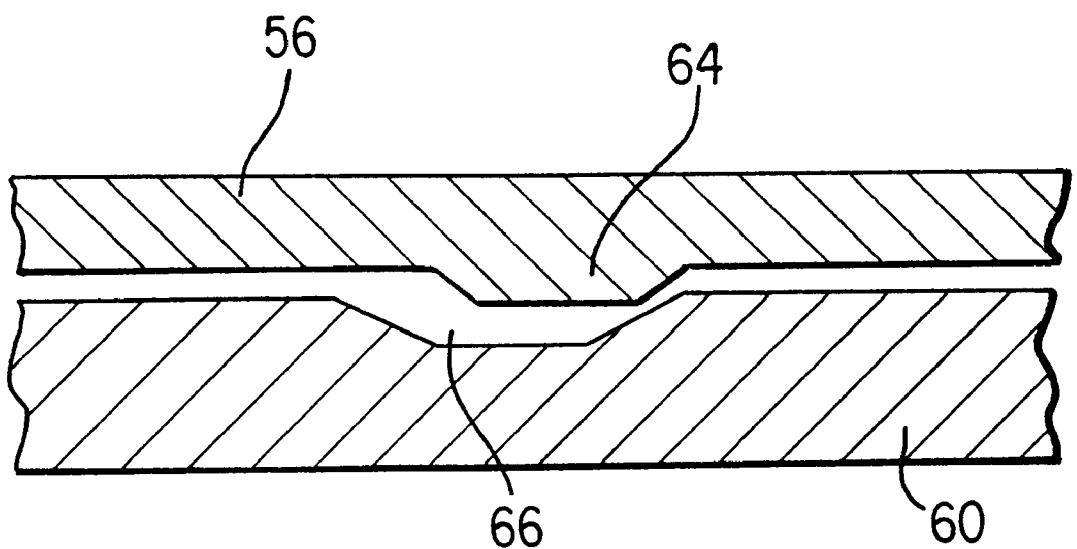
FIG. 11 is a cross-sectional view taken along line 11—11 of FIG. 10.

Upon rotation of the first cap member 56 and the second cap member 60 relative to each other about the threaded connection, the overall length of the cap 50 is increased or decreased depending upon the direction of rotation. During rotation, the protruding elements 64 snap into and out of the recesses 66 of threads 62 of the second cap member 60 such that the length of the cap 50 may be fixed at a particular length by leaving the protruding elements 64 engaged in particular recesses 66, (FIG. 11).

FIG. 3B shows the needle holding member 30 in its fully extended position with the length of the cap 50 adjusted such that the disposable lancet 70 strikes the cap 50 in the fully extended position.

FIG. 3C also illustrates the needle holding member 30 in its fully extended position. The length of the cap 50, however, has been extended such that the disposable lancet 70 does not strike the cap 50 in the fully extended position. Thus, adjusting the length of the cap 50 adjusts the penetration depth of the disposable lancet 70.

The overall sliding and axial movement of the needle holding member 30 is regulated by a stopper system. In the preferred embodiment, detailed in FIG. 2, the stopper system includes a guide collar 28 disposed within the housing 20. The guide collar 28 is adapted to receive the distal segment 32 of the needle holding member 30 slidably therethrough. The needle holding member 30 is preferably flat such that it will slide through the guide collar 28, but will not rotate axially therein, thereby assuring that the needle holding member 30 will remain properly oriented when moved into its cocked, retracted position. Further, the guide collar 28 is sized to retain a flanged end 33 of the distal segment 32 of the needle holding member 30 between the closed first end 22 of the housing 20 and the guide collar 28. In this manner, inward movement of the needle holding member within the housing 20 is limited by the flanged end 33 contacting the closed first end 22 of the housing 20, and outward movement of the needle holding member 20 is limited by the flanged end 33 of the distal segment 32 contacting the guide collar 28. In this manner, the needle holding member 30 will be retained within the channel 26.

Turning to FIG. 8, an alternative embodiment of the stopper system includes an elongate slot 33' disposed in the distal segment 32 of the needle holding member 30. The slot is positioned such that a peg 28' which extends from an interior of the housing 20 passes therethrough. The peg 28' remains within the elongate slot 33' at all times thereby limiting movement of the needle holding member 30 to a length of the slot 33' and assuring that the needle holding member 30 is retained within the channel 26 of the housing 20. Also, positioning of the peg 28' within the slot 33' will not allow axial rotation of the needle holding member 30.

Although the stopper systems of FIGS. 7 and 8 involve an interaction between the distal segment 32 of the needle holding member 30 and a stationary element, the stopper system could involve an interaction between another segment of the needle holding member and a stationary element. For instance, the stopper system could involve interaction of the central segment 35 with an element attached to the housing 20.

To move the needle holding member 30 from its cocked, retracted position to its fully extended position, a biasing element is included. While other types of biasing elements may be used, the biasing element is preferably in the form of a coil spring 40 disposed about the distal segment 32 of the needle holding member 30. Other types of springs which may be useful as biasing elements include leaf springs and C-springs. The spring 40 is positioned such that it will abut a flanged lip 34 formed in the needle holding member 30 and will abut the housing 20. Preferably, a side of the spring 40 which abuts the housing 20 will have a larger relaxed diameter than an opposite side of the spring 40. In a first embodiment, illustrated in FIG. 2, one end of the spring 40 is positioned to contact the guide collar 28 of the housing 20 and is preferably embedded in an annular ridge 42 formed in the housing 20. The opposite side of the spring 40, which abuts the needle holding member 30 is preferably contained within an annular ridge 43 formed at the flanged lip 34. In the embodiment of FIGS. 1–7, the spring 40 abuts the housing 20 at peg 28' which is positioned through the slot 33' in the distal segment 32 as shown in FIG. 5. In an alternative embodiment illustrated in FIG. 8, the spring 40 abuts peg 28" which is also positioned through the slot 33' in the distal segment 32.

With the spring 40 positioned appropriately, when extended, the spring 40 will urge the needle holding member 30 toward the open second end 24 of the housing 20. When the needle holding member 30 is in its retracted, cocked position, as detailed in FIG. 2, the spring 40 is compressed. Once the needle holding member 30 is allowed to move to its extended position, the spring 40 will quickly and immediately move the needle holding member 30 to the fully extended position with the point 71 of the disposable lancet 70 protruding through the piercing opening 53 to puncture a desired surface. Depending upon how the length of the cap 50 is set, the disposable lancet 70 will strike the cap 50, (see FIG. 3B), or will not strike the cap 50, (see FIG. 3C), in the fully extended position.

After this initial release and movement to the fully extended position, the spring 40 relaxes such that the needle holding member 30 will move slightly back toward the closed first end 22 of the housing 20, as illustrated in FIG. 3D, into a relaxed position wherein the point 71 of the disposable lancet 70 is contained within the cap 50 and will not accidentally contact a user unnecessarily.

In order to hold the needle holding member 30 in its cocked, retracted position, and subsequently allow release by a user in order to initiate movement of the needle holding member 30 to its extended position, a trigger is included. The trigger preferably includes an aperture 29 formed in the housing 20 near the open second end 24 thereof. Also included as part of the trigger is an outwardly biased engagement segment 36 which extends from the central segment 35 of the needle holding member 30. The engagement segment 36 includes a distal lip segment 37 which contacts an interior of the housing 20 as the needle holding member 30 slides within the channel 26. Contact is made due to the outwardly biasing nature of the engagement segment 36, and when the needle holding member 30 is pushed into the housing 20 so as to be in its retracted, cocked position, the distal lip segment 37 extends upwardly into the aperture 29 formed in the housing 20 so as to contact the housing 20 inside the aperture 29 and maintain the needle holding member 30 in its retracted, cocked position and the spring 40 in its compressed position.

In order to release the needle holding member 30 from its retracted, cocked position, the engagement segment 36 must be pushed such that the distal lip segment 37 exits the aperture 29 and the needle holding member 30 can move freely to its fully extended position due to the biasing force of the spring 40. In order to push the engagement segment 36, a trigger button 45 is disposed within the aperture 29. The trigger button 45, as detailed in FIG. 4, includes an upper section 46 which protrudes through the aperture 29 to an exterior of the housing 20 and a flanged base portion 47 which is disposed within the housing 20 so as to assure that the trigger button 45 does not get pushed out of the housing 20 through the aperture 29. Disposed within the base 47 is a channel 48 positioned such that the distal lip segment 37 of the engagement segment 36 will slide therethrough and be able to engage the housing 20 within the aperture 29.

Figure 12:
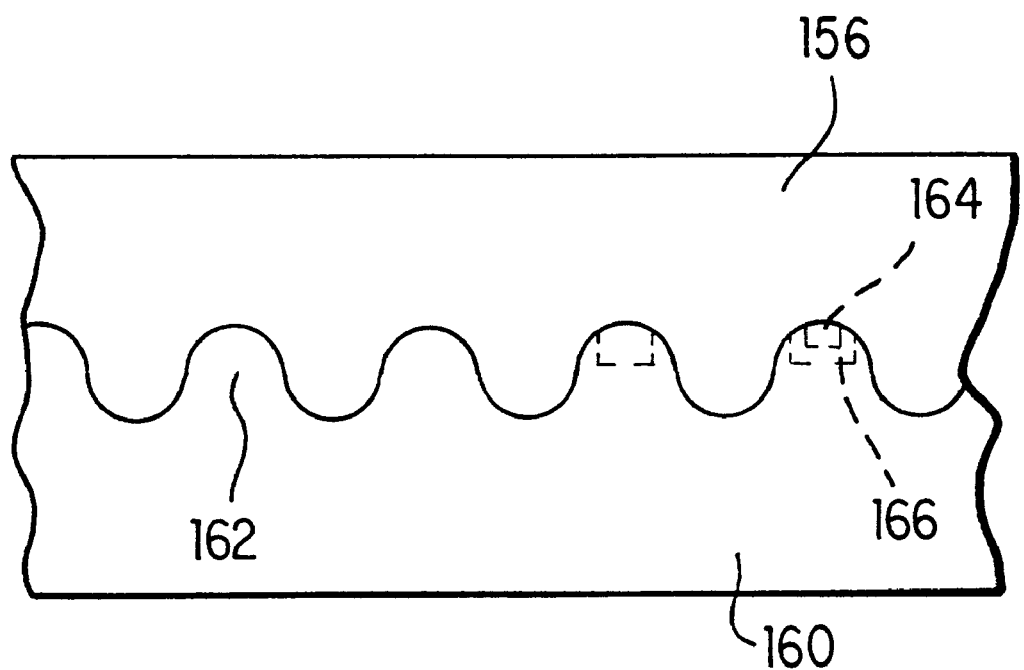
FIG. 12 is a cross-sectional view similar to FIG. 10 showing another embodiment of the present invention with recesses in ridges of threads of the second cap member.

Although the recesses 66 shown in the embodiments of FIGS. 1–11 are disposed in a groove formed by threads 62 of the second cap member 60, recesses 166 could be disposed in a ridge formed by threads 162 of the second cap member 160 (FIG. 12). The threads 162 of the second cap member 160 interact with the first cap member 156.

Figure 13:
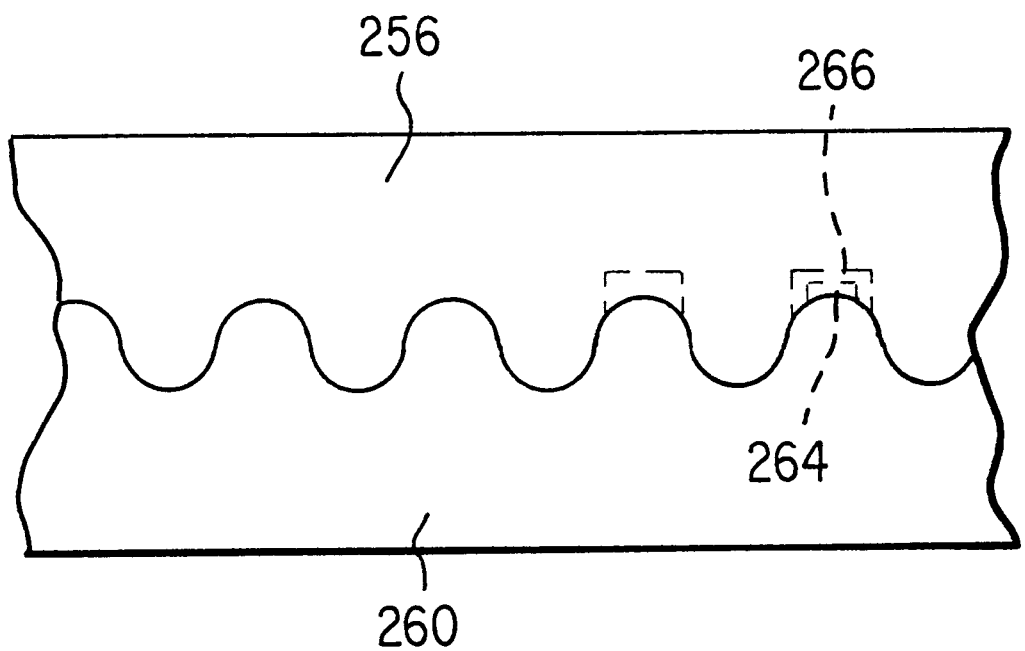
FIG. 13 is a cross-sectional view similar to FIGS. 10 and 12 showing yet another embodiment of the present invention with recesses in threads of the first cap member.

Further, although the recesses 66 shown in the embodiments of FIGS. 1–11 are disposed in the second cap member 60 and the protruding elements 64 are part of the first cap member 56, the recesses and grooves could be reversed. In this regard, recesses 266 are disposed in the first cap member 256 and the protruding elements 264 could be part of the second cap member 260 (FIG. 13).

Figure 14:
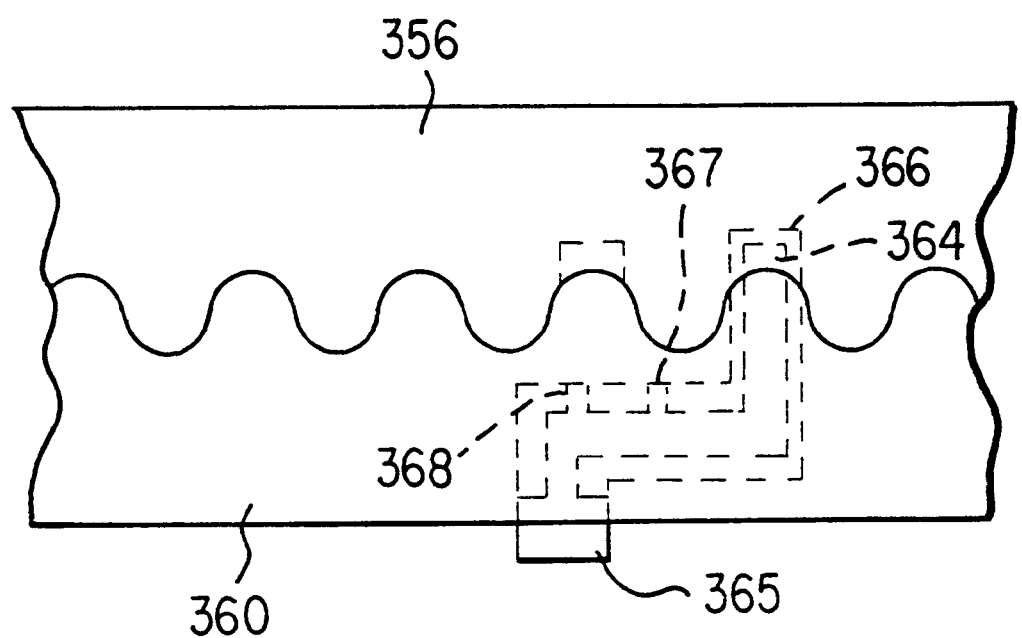
FIG. 14 is a cross-sectional view similar to FIGS. 10, 12, and 13 showing still another embodiment of the present invention with a button in the second cap member.

FIG. 14 shows another embodiment where the protruding elements 364 are connected to a button 365 which facilitates disengagement of the protruding element 364 from the recesses 366. Between the button 365 and the protruding element 364 is a pivot 367 about which the protruding element 364 and the button 365 pivot. Thus, when the button 365 is depressed, the protruding element 364 is removed from the recess 366 to allow the first cap member 356 to be rotated relative to the second cap member 360 to allow adjustment of the length of the cap. When the button 365 is released, the protruding element 364 is biased into recesses 366 by the natural memory of the material of the button 365 and protruding element 364 or by a spring 368 disposed under the button 365.

Figure 15:
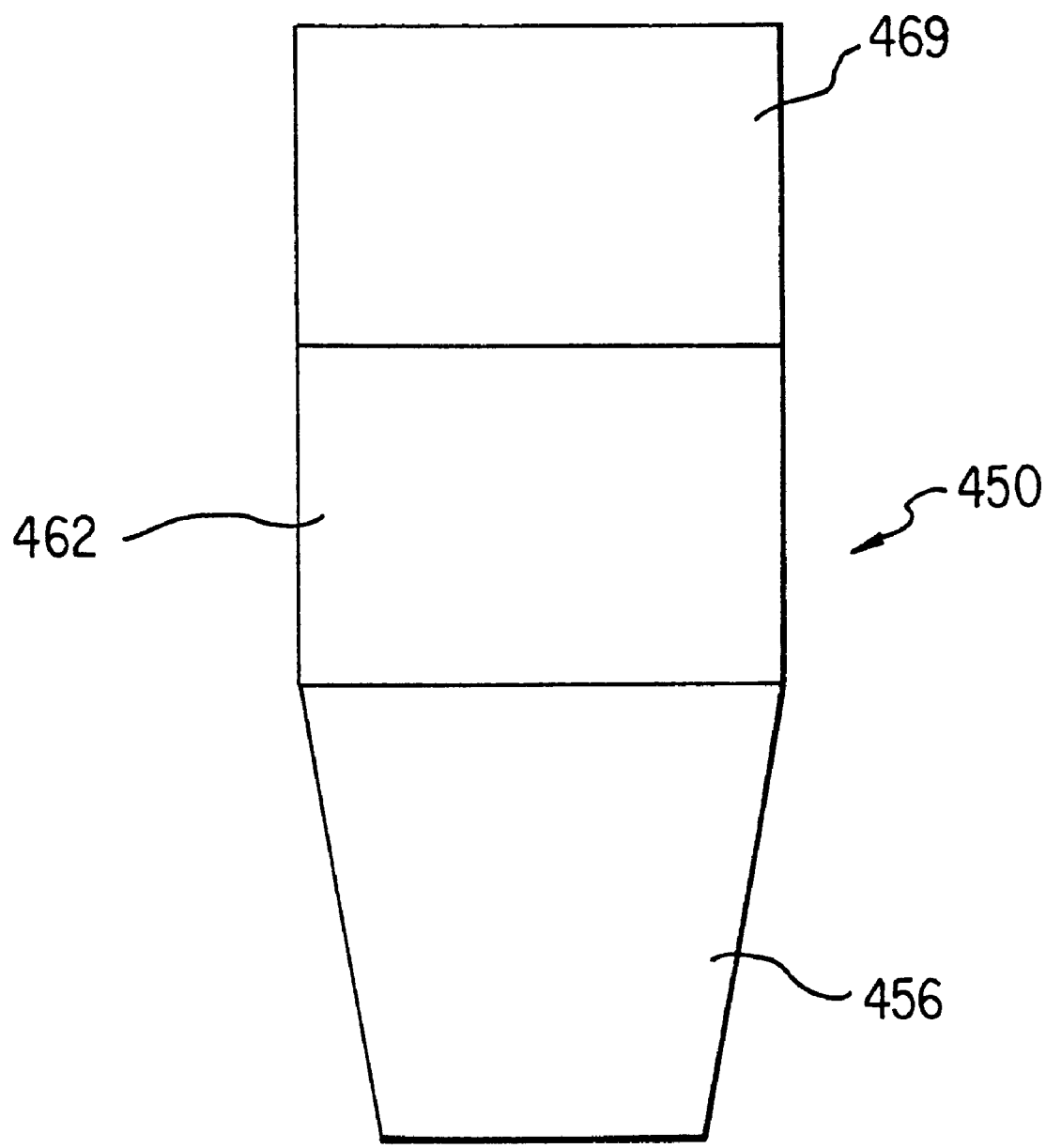
FIG. 15 is a view of a cap having three cap members.

FIG. 15 shows yet another embodiment wherein a cap 450 has a first cap member 456, a second cap member 462, and a third cap member 469. As a result, the length of the cap member 450 can be adjusted by adjusting the connection between either the first cap member 456 and the second cap member 462 or the connection between the second cap member 462 and the third cap member 469 or both. In this regard, the cap may have more than three cap members to adjust the length of the cap.

The reusable lancet device 10 of the present invention includes a relatively small number of distinct pieces. The use of such a small number of pieces enables quick and substantially inexpensive manufacturing of the reusable lancet device 10 of the present invention, thereby making a cost effective product which can be available to the public without compromising safety.

During use, the needle holding member 30 is moved to its retracted, cocked position by removing the cap 50, placing the disposable lancet 70 within the needle holding member 30, and pushing the disposable lancet 70 and accordingly the needle holding member 30 into the housing 20 until the trigger engages. Once properly positioned, the protective cap 72 can be removed from the disposable lancet 70 so as to expose the point 71, and the cap 50 is replaced thereover. Due to the triangular shape, the cap 50 will securely and properly fit over the housing 20 no matter which orientation a user utilizes to push the cap 50 onto the housing 20. After a single use of the disposable lancet 70, the cap 50 is removed, the disposable lancet 70 is removed and discarded appropriately, and the reusable lancet device 10 of the present invention is ready for an additional use.

When a user wishes to adjust the length of the cap 50, the user simply rotates the distal cap segment relative to the proximal cap segment such that the protruding element snaps into and out of individual threads. To fix the length of the cap, the user leaves the protruding element engaged in a particular thread. The reusable lancet device is then ready for use. At this point, it should be noted that once the user adjusts the penetration depth to an appropriate depth, the penetration depth usually does not need to be adjusted again.

From the above discussion and from the drawings, it is clear that the at least one protrusion may be stationarily fixed within the threads of one of the first member and the second member, such as the first cap member and the second cap member. In this regard, even if the at least one protrusion is stationarily fixed on one of the first member and the second member, since the at least one protrusion may be composed of a resilient material, as discussed above, such as plastic, as discussed below, the at least one protrusion is preferably resilient and capable of flexing. Similarly, the at least one stop may be fixed within the threads of the other of the first member and the second member, such as the first cap member and the second cap member.

Preferably, the components of the reusable lancet device of the present invention are made of plastic. Examples of desirable include polyproylene (PP), polyvinyl chloride (PVC), acrylonitrile butadiene styrene (ABS), nylon, linear polyoxymethylene-type acetal resin, e.g., "DELRIN", and polycarbonate (PC), e.g., "LEXAN".

To assist in determining the penetration depth of the lancet, indicia can be included on members that change position relative to each other when the penetration depth is adjusted. For example, as illustrated in FIG. 1, indicia 87 and 88 can be included on first cap member 56 and second cap member 60. The indicia can comprise elements which can be viewed by shape and/or color, such as reference numerals, letters, lines and geometric shapes. Moreover, the indicia may be sensed by touch, such as raised elements, including braille. As illustrated, indica 87 includes a line and indicia 88 includes reference numerals. The reference numerals can be numbers, such as from 0 to 5, with 0 being no penetration to 5 being maximum penetration.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed:

1. An adjustable length element, comprising:
   a first member having threads;
   a second member having threads;
   at least one protrusion stationarily fixed within the threads of one of the first member and the second member, the at least one protrusion being capable of engaging and disengaging at least one stop within the threads of the other of the first member and the second member as the first member and the second member are rotated relative to each other; and
   wherein the first member and the second member are rotatable relative to each other in both a clockwise and a counter-clockwise direction.

2. The adjustable length element of claim 1, wherein the at least one stop comprises at least one recess.

3. The adjustable length element of claim 1, wherein the at least one stop comprises at least one projection.

4. The adjustable length element of claim 1, wherein the threads of the other of the first member and the second member comprise a groove and a ridge, and wherein the at least one stop is located in the groove.

5. The adjustable length element of claim 1, wherein the threads of the other of the first member and the second member comprise a groove and a ridge, and wherein the at least one stop is located in the ridge.

6. The adjustable length element of claim 1, wherein the at least one protrusion is connected to a button for releasing the at least one protrusion from the at least one stop.

7. The adjustable length element of claim 6, wherein the at least one protrusion is biased into the at least one stop.

8. The adjustable length element of claim 1, wherein the at least one stop is fixed on the other of the first member and the second member.

9. A lancet device, comprising:
   a housing;
   a needle holding member in the housing for holding a lancet;
   a biasing element for biasing the needle holding member toward an extended position;
   a trigger for releasing the needle holding member from a retracted position; and
   a cap for covering the housing and for positioning the lancet device relative to a skin surface, the cap comprising a first cap member having threads and a second cap member having threads, the cap further comprising at least one protrusion stationarily fixed within the threads of one of the first cap member and second cap member, the at least one protrusion being capable of engaging and disengaging at least one stop within the threads of the other of the first cap member and the second cap member as the first cap member and the second cap member are rotated relative to each other.

10. The lancet device of claim 9, wherein the at least one stop comprises at least one recess.

11. The lancet device of claim 9, wherein the at least one stop comprises at least one projection.

12. The lancet device of claim 9, wherein the threads of the other of the first member and the second member comprise a groove and a ridge, and wherein the at least one stop is located in the groove.

13. The lancet device of claim 9, wherein the threads of the other of the first member and the second member comprise a groove and a ridge, and wherein the at least one stop is located in the ridge.

14. The lancet device of claim 9, wherein the at least one protrusion comprises a nipple.

15. The lancet device of claim 9, wherein the at least one protrusion comprises a spring-biased ball.

16. The lancet device of claim 9, wherein the at least one protrusion is on an interior of the cap.

17. The lancet device of claim 9, wherein the at least one protrusion comprises a plurality of protrusions.

18. The lancet device of claim 9, wherein the first cap member comprises a surface for aligning the lancet device on skin of a patient, the surface having an opening for a needle in the needle holding member to pass through, and wherein the at least one protrusion is on the second cap member.

19. The lancet device of claim 9, wherein the first cap member comprises a surface for aligning the lancet device on skin of a patient, the surface including an opening for a needle in the needle holding member to pass through, and wherein the at least one protrusion is on the first cap member.

20. The lancet device of claim 9, wherein a length of the cap is adjustable by rotation of the first cap member relative to the second cap member for adjusting a penetration depth of a needle in the needle holding member.

21. The lancet device of claim 9, wherein the at least one protrusion is connected to a button for releasing the at least one protrusion from the at least one stop.

22. The lancet device of claim 9, wherein the at least one protrusion is biased into the at least one stop.

23. The adjustable length element of claim 1, wherein each of the at least one protrusion is formed on one of a single groove and a single ridge of the threads of one of the first member and the second member;
   wherein when one of the at least one protrusion is formed on a said single groove of one of the first member and the second member, a corresponding at least one stop is formed on a ridge of the threads of the other of the first member and the second member; and
   wherein when one of the at least one protrusion is formed on a said single ridge of one of the first member and the second member, a corresponding at least one stop is formed on a groove of the threads of the other of the first member and the second member.

24. The lancet device of claim 9, wherein the first cap member and the second cap member are rotatable relative to each other in both a clockwise and a counter-clockwise direction.

25. The lancet device of claim 9, wherein each of the at least one protrusion is formed on one of a single groove and a single ridge of the threads of one of the first cap member and the second cap member;
   wherein when one of the at least one protrusion is formed on a said single groove of one of the first cap member and the second cap member, a corresponding at least one stop is formed on a ridge of the threads of the other of the first cap member and the second cap member; and
   wherein when one of the at least one protrusion is formed on a said single ridge of one of the first cap member and the second cap member, a corresponding at least one stop is formed on a groove of the threads of the other of the first cap member and the second cap member.

26. The lancet device of claim 9, wherein the at least one stop is fixed on the other of the first cap member and the second cap member.

* * * * *